United States Patent
Mohan et al.

(10) Patent No.: US 9,556,124 B2
(45) Date of Patent: Jan. 31, 2017

(54) METHODS FOR REMOVING TRIAZINE FROM N-METHYLIMIDAZOLE FOR SYNTHESIS OF OLIGONUCLEOTIDE

(71) Applicant: Honeywell International Inc., Morristown, NJ (US)

(72) Inventors: Venkatraman Mohan, Muskegon, MI (US); Sandra M. Lorenz, Grand Haven, MI (US); Gregory Gajda, Mt. Prospect, IL (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 190 days.

(21) Appl. No.: 14/471,635

(22) Filed: Aug. 28, 2014

(65) Prior Publication Data
US 2015/0119564 A1    Apr. 30, 2015

Related U.S. Application Data

(60) Provisional application No. 61/897,886, filed on Oct. 31, 2013.

(51) Int. Cl.
| | |
|---|---|
| C07H 21/00 | (2006.01) |
| C07D 233/00 | (2006.01) |
| C07D 233/58 | (2006.01) |
| C07H 1/00 | (2006.01) |
| C07H 21/04 | (2006.01) |

(52) U.S. Cl.
CPC ............... *C07D 233/58* (2013.01); *C07H 1/00* (2013.01); *C07H 21/04* (2013.01)

(58) Field of Classification Search
CPC .......... C07D 233/58; C07H 21/04; C07H 1/00
See application file for complete search history.

(56) References Cited

U.S. PATENT DOCUMENTS

| | | | |
|---|---|---|---|
| 5,998,604 | A | 12/1999 | Fearon et al. |
| 8,039,612 | B2 | 10/2011 | Lorenz et al. |
| 2001/0044529 | A1 | 11/2001 | Beaucage et al. |
| 2004/0035690 | A1 | 2/2004 | Gulari |
| 2009/0099352 | A1 | 4/2009 | Lorenz et al. |

FOREIGN PATENT DOCUMENTS

JP    2007238499 A    9/2007

OTHER PUBLICATIONS

Written Opinion and International Search Report mailed Mar. 18, 2015 in International Application No. PCT/US2014/059410.
Zhang, L. et al., "Thermal detemplation of Na-SAPO-34: Effect on Sr2+ ion exchange and CO2 adsorption". The Journal of Physical Chemistry C. Epub. Aug. 13, 2010, vol. 114, No. 35, pp. 14755-14762.

*Primary Examiner* — Lawrence E Crane
(74) *Attorney, Agent, or Firm* — Lorenz & Kopf, LLP

(57) ABSTRACT

Methods for removing 1,3,5-trimethylhexahydro-1,3,5-triazine and N-methylenemethanamine from a N-methylimidazole and methods for making oligonucleotides using N-methylimidazole are provided. In one embodiment, a method for removing 1,3,5-trimethylhexahydro-1,3,5-triazine and N-methylenemethanamine from a feedstock containing N-methylimidazole includes contacting the feedstock with small or medium pore molecular sieves. The small or medium pore molecular sieves adsorb 1,3,5-trimethylhexahydro-1,3,5-triazine and N-methylenemethanamine from the feedstock. The method further includes separating the small or medium pore molecular sieves from the feedstock.

10 Claims, 10 Drawing Sheets

1,3,5-trimethylhexahydro-1,3,5-triazine

3 CH$_2$ = N — Me

N-methylenemethanamine oligo ⟶ oligo + 85 Daltons

METHODS FOR REMOVING TRIAZINE FROM N-METHYLIMIDAZOLE FOR SYNTHESIS OF OLIGONUCLEOTIDE

CROSS-REFERENCE TO RELATED APPLICATION

This application claims priority to and the benefit of U.S. Provisional Application No. 61/897,886, filed on Oct. 31, 2014 in the U.S. Patent and Trademark Office.

TECHNICAL FIELD

The technical field generally relates to methods for purifying N-methylimidazole, and more particularly relates to methods for removing triazine from N-methylimidazole.

BACKGROUND

N-methylimidazole may be used to synthesize oligonucleotides and/or phosphorothioate oligonucleotides. The synthesis generally has the following steps: (a) deblocking, (b) activation/coupling, (c) capping, and (d) oxidizing (in the case of oligonucleotides) or sulfurizing (in the case of phosphorothioate oligonucleotides). The cycle may be repeated sequentially depending on the number of bases to be coupled. The capping step is commonly carried out in the presence of a combination of N-methylimidazole and acetic anhydride. In some oligonucleotide syntheses employing N-methylimidazole, it has been observed that unwanted adducts may form. The adducts have been observed to add 85 daltons to the molecular weight of the oligonucleotides.

It has been determined that the formation of unwanted adducts occurs when the N-methylimidazole includes 1,3,5-trimethylhexahydro-1,3,5-triazine as an impurity. Specifically, 1,3,5-trimethylhexahydro-1,3,5-triazine has been found to react with the oligonucleotide to form unwanted adducts. Therefore, it would be beneficial to provide a method for removing 1,3,5-trimethylhexahydro-1,3,5-triazine from N-methylimidazole. Use of 1,3,5-trimethylhexahydro-1,3,5-triazine-free N-methylimidazole may provide for optimized synthesis of oligonucleotides and/or phosphorothioate oligonucleotides.

Accordingly, it is desirable to provide a method for removing 1,3,5-trimethylhexahydro-1,3,5-triazine from N-methylimidazole. Further, it is desirable to provide a method for forming oligonucleotides that includes the step of removing 1,3,5-trimethylhexahydro-1,3,5-triazine from N-methylimidazole before using the N-methylimidazole to cap unreacted deblocked nucleotide. Furthermore, other desirable features and characteristics will become apparent from the subsequent detailed description and the appended claims, taken in conjunction with the accompanying drawings and the foregoing technical field and background.

BRIEF SUMMARY

Methods for removing 1,3,5-trimethylhexahydro-1,3,5-triazine from N-methylimidazole and methods for making oligonucleotides using N-methylimidazole are provided. In an exemplary embodiment, a method for removing 1,3,5-trimethylhexahydro-1,3,5-triazine from a feedstock containing N-methylimidazole includes contacting the feedstock with small or medium pore molecular sieves. The small or medium pore molecular sieves adsorb 1,3,5-trimethylhexahydro-1,3,5-triazine from the feedstock. The method further includes separating the small or medium pore molecular sieves from the feedstock.

In another embodiment, a method for making oligonucleotides includes preparing an amount of N-methylimidazole substantially free of 1,3,5-trimethylhexahydro-1,3,5-triazine. The method prepares the amount of N-methylimidazole by contacting a feedstock of N-methylimidazole with small or medium pore molecular sieves that adsorb 1,3,5-trimethylhexahydro-1,3,5-triazine from the feedstock, and by separating the small or medium pore molecular sieves from the feedstock. The method further includes deblocking blocked nucleotide having a dimethoxytrityl group blocking a 5'-hydroxyl group. Also, the method includes activating the deblocked nucleotide, and reacting deblocked nucleotide with a phosphoramidite to form phosphite oligomer. The method further includes capping unreacted deblocked nucleotide by reacting the unreacted deblocked nucleotide with an amount of acetic anhydride and the amount of N-methylimidazole substantially free of 1,3,5-trimethylhexahydro-1,3,5-triazine.

DETAILED DESCRIPTION

Figure 1:
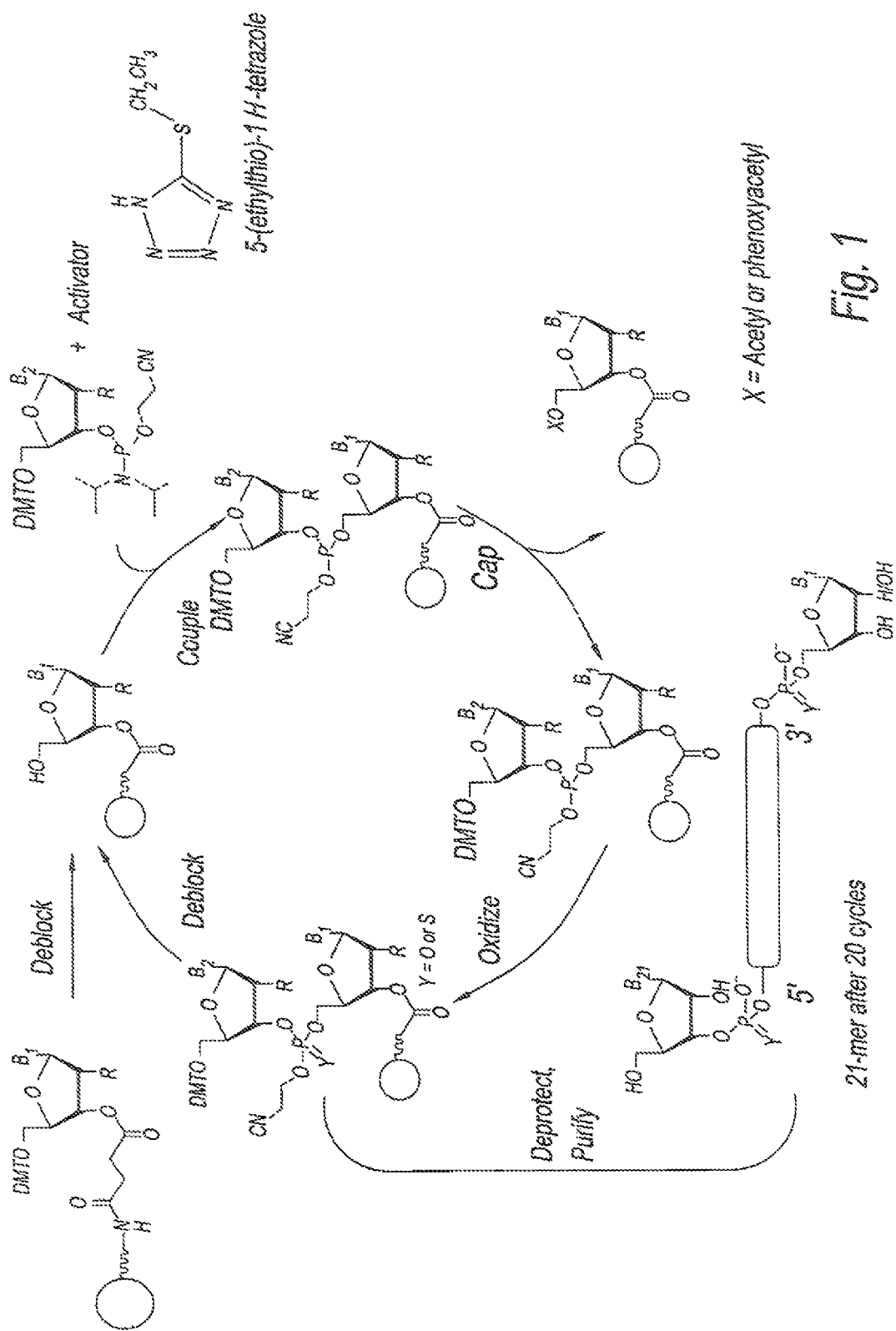
FIG. 1 is a representation of an embodiment of a method for forming oligonucleotides in accordance with an embodiment herein.

Unwanted adducts formed during synthesis of oligonucleotides have been identified as an impurity in N-methylimidazole and result from one of the capping agents used in the synthesis processes. The impurity has been found in some industrial lots of N-methylimidazole as 1,3,5-trimethylhexahydro-1,3,5-triazine and/or its Schiff base, N-methylenemethanamine. The two impurities are usually present in equilibrium in N-methylimidazole. For purposes of convenience and easy reference, 1,3,5-trimethylhexahydro-1,3,5-triazine and its Schiff base, N-methylenemethanamine, are referred to and claimed singularly herein as 1,3,5-trimethylhexahydro-1,3,5-triazine. Other names for the impurities include s-triazine; hexahydro-1,3,5-trimethyl-s-triazine; 1,3,5-trimethylhexahydro-s-triazine; 1,3,5-trimethylhexahydro-sym-triazine; and hexahydro-1,3,5-trimethyl-1,3,5-triazine. The triazine content in N-methylimidazole has been observed to be as high as about 1500 parts per million (ppm), and in a range of about 20 ppm to 1000 ppm such as about 400 ppm to about 800 ppm. The triazine may be identified in N-methylimidazole with analytical techniques such as gas chromatograph mass spectroscopy (GCMS) and proton NMR.

As described herein, and in particular in reference to FIG. 13 below, the problem of impure N-methylimidazole is resolved by removing triazine from industrial lots of N-methylimidazole. Preferably, after removal, the N-methylimidazole has about 20 ppm or less, such as about 10 ppm or less, of the triazine by weight based on the weight of the N-methylimidazole. Most preferably, after removal, the N-methylimidazole has about 1 ppm or less of the triazine.

In a first step of the oligonucleotide synthesis process, a blocked nucleotide is provided. The initial blocked nucleotide is preferably provided in a form covalently linked to a support, such as silica or a polymer. The blocked nucleotide is variously derived and selected from among available heterocyclic nucleic acid bases. The blocked nucleotide is deblocked to form a deblocked nucleotide. In one embodiment, the deblocking is carried out via reaction with an amount of dichloroacetic acid in the presence of toluene or dichloromethane.

The deblocked nucleotide is then activated to prepare it for coupling with a phosphoramidite. Activation is carried out via contact with an activator.

After activation, the deblocked nucleotide is coupled, i.e., reacted, with a phosphoramidite to form a phosphite oligomer. The phosphoramidite is variously selected from among all available phosphoramidites. In an exemplary formation of useful oligonucleotides, the deblocking step, coupling step, capping step, and oxidizing or sulfurizing step is repeated until the desired oligonucleotide length is achieved.

Typically, during the coupling step, only a portion of the deblocked nucleotide reacts with the phosphoramidite. The unreacted nucleotides must be capped. Capping is carried out by reacting the unreacted nucleotides with an amount of acetic anhydride and an amount of N-methylimidazole that is substantially free of 1,3,5-trimethylhexahydro-1,3,5-triazine. The capped oligonucleotides are no longer available for subsequent nucleotide additions.

After capping, the phosphite oligomer is oxidized or sulfurized. In one embodiment of the process, the phosphite oligomer is oxidized via reaction with iodine in the presence of water and pyridine.

The features of the method for synthesizing oligonucleotides will be made more apparent by the following examples, which are not to be construed as limiting.

Example 1

Oligonucleotides can be synthesized while using a capping agent of N-methylimidazole substantially free of 1,3,5-trimethylhexahydro-1,3,5-triazine according to an exemplary embodiment.

Figure 2:
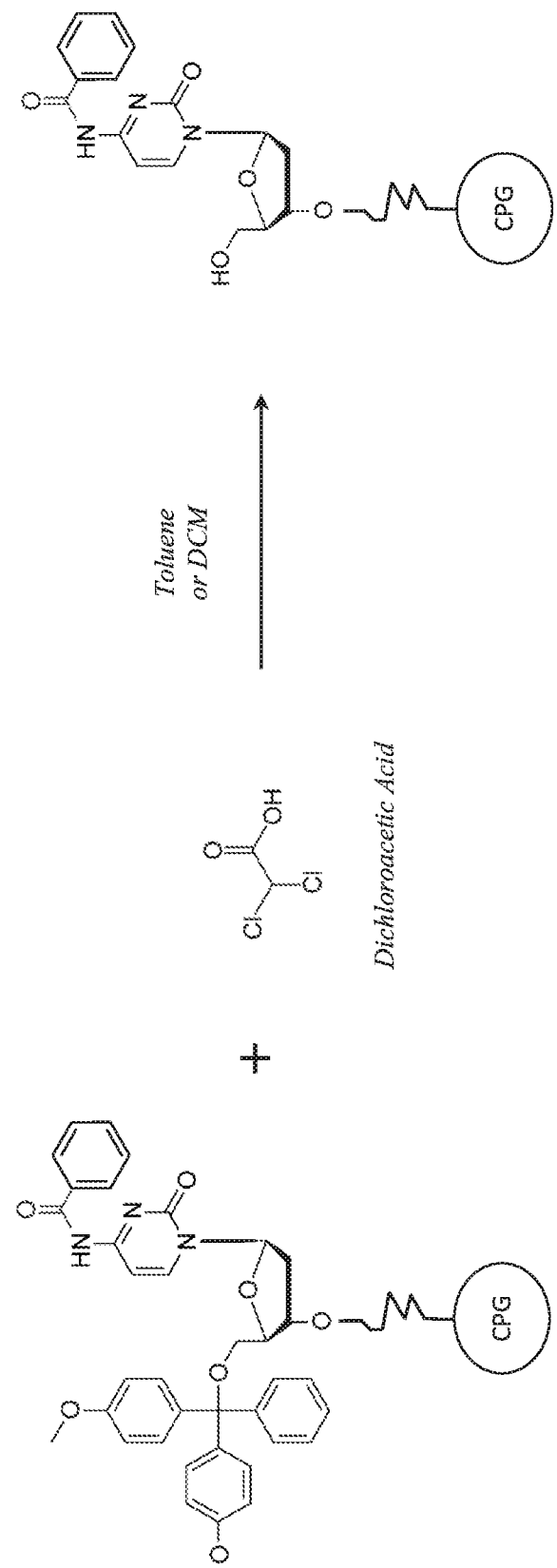
FIG. 2 is a representation of a deblocking step of the oligonucleotides synthesis process.

Referring to FIG. 2, the first base, a cytidine nucleotide, which is attached to a CPG solid support, is at first inactive because all the active sites have been protected. To add the next base, the dimethoxytrityl (DMT) group protecting the 5'-hydroxyl group must be removed (the deblocking step). Addition of 3% DCA in DCM (or in toluene) removes the DMT group and allows the 5'-hydroxyl group to become the reactive site.

Figure 3:
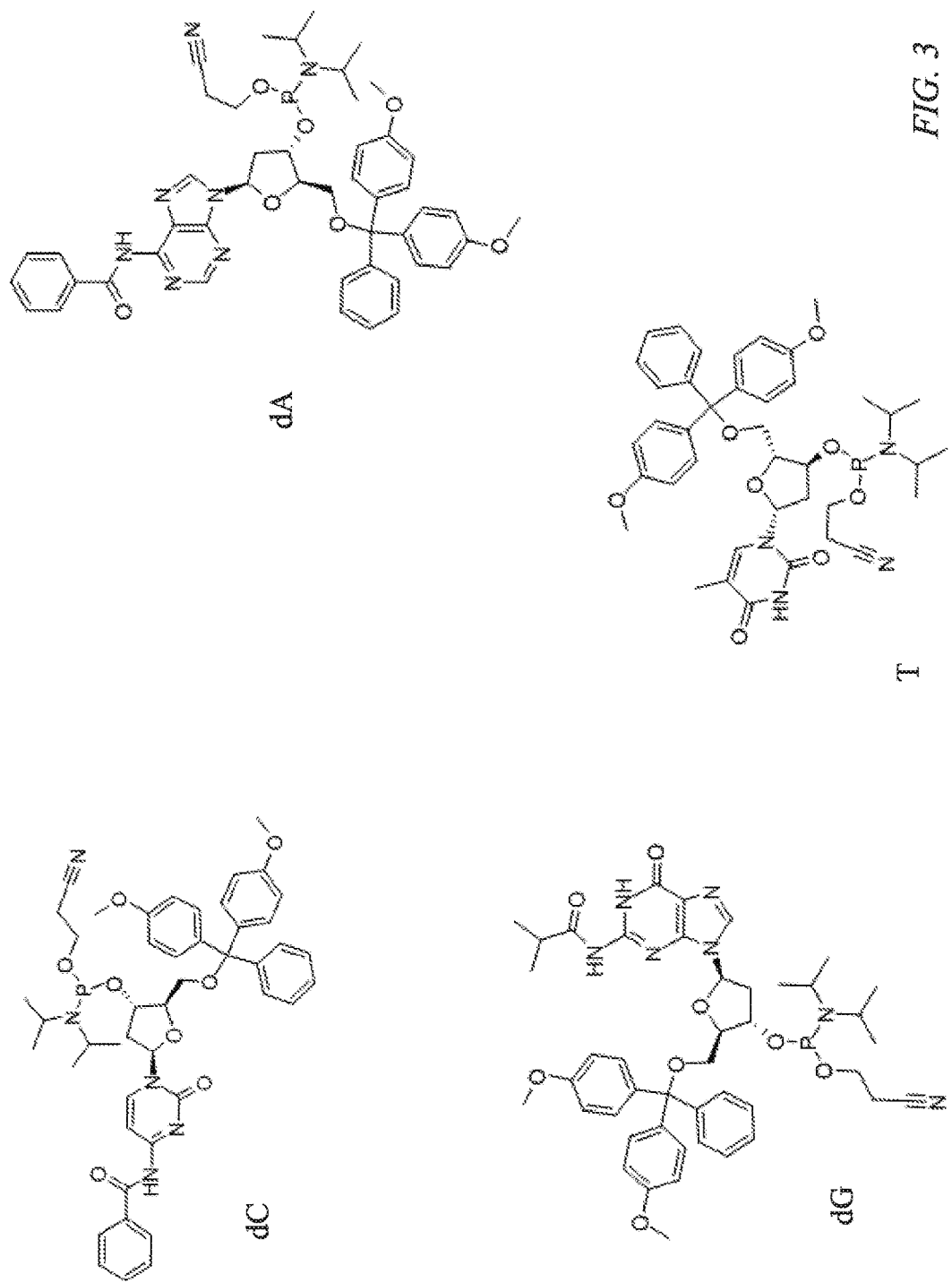
FIG. 3 is a representation of chemical structures of DMT-protected phosphoramidites (dC, dA, T and dG) with appropriate protecting groups on the heterocyclic bases.

The next base monomer cannot be added until it has been activated (the activation step). This is achieved by adding an activator, such as a tetrazole-based activator, for instance, 5-ethylthiotetrazole, to the column. The active 5'-hydroxyl group of the preceding base and the newly activated phosphorus bind to loosely join the two bases together. This forms an unstable phosphite linkage. The reaction column is then washed with acetonitrile to remove any extra activator, unbound phosphoramidite and by-products. There are four DMT-protected nucleotides (phosphoramidites) that are depicted in FIG. 3.

Figure 4:
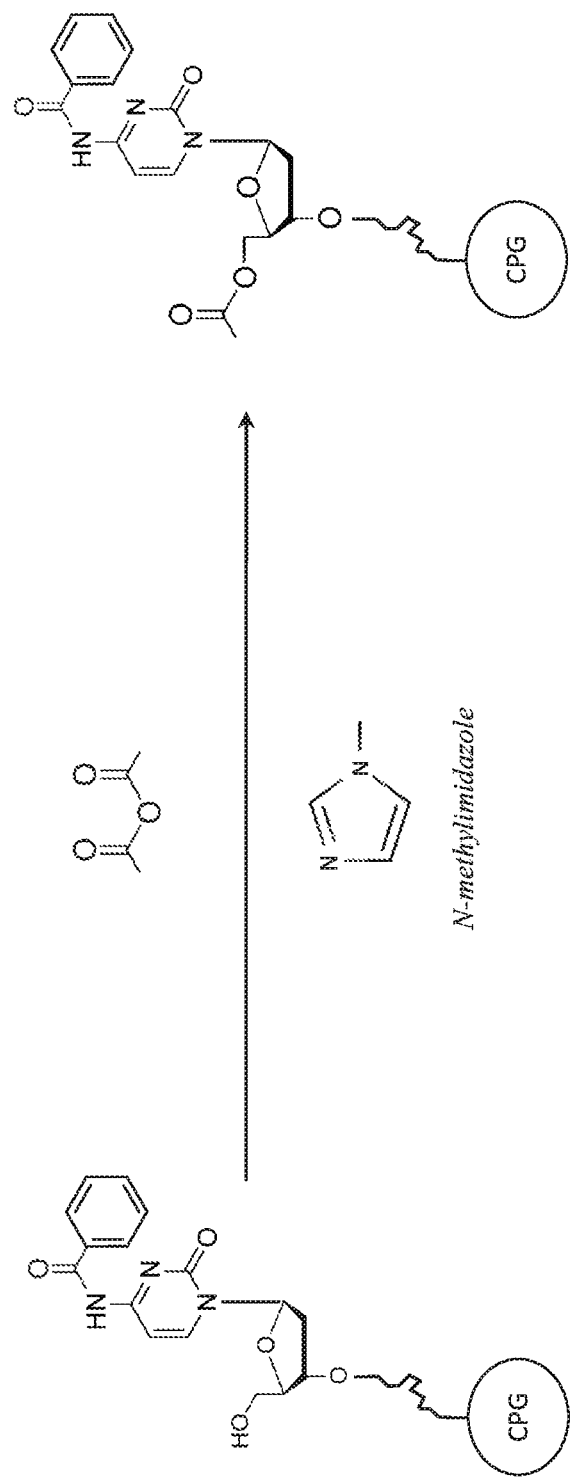
FIG. 4 is a representation of a capping step of the oligonucleotides synthesis process.

Any of the first bases that fail to react are capped with NMI as depicted in FIG. 4 (the capping step). These failed bases are expected to play no further part in the synthesis cycle. The base on the left (already attached to the solid support) did not bind to a base in the activation step. The unreacted 5'-hydroxyl is blocked from further reactions by acetylation.

In the activation step, the next desired base is added to the previous base, which results in an unstable phosphite linkage. To stabilize this linkage, an oxidizing solution of dilute iodine in water and pyridine is added to the reaction column. The unstable phosphite linkage is oxidized to form a more stable phosphate linkage (the oxidation step).

Figure 5:
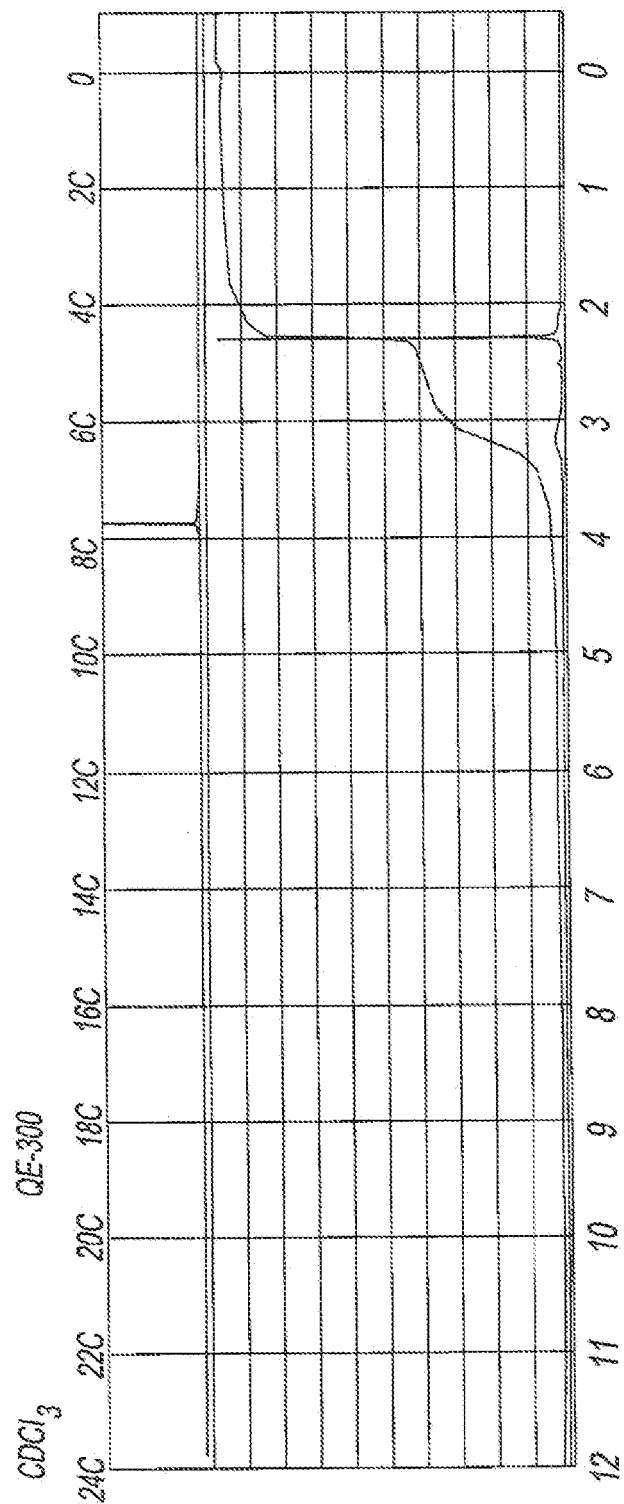
FIG. 5 is a representation of an 1H NMR spectra of 1,3,5-trimethylhexahydro-1,3,5-triazine.
Figure 8:
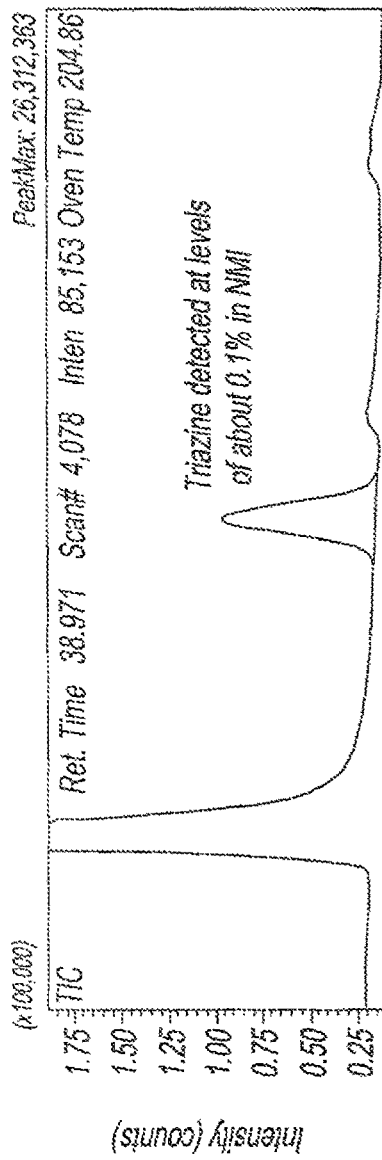
FIGS. 8 to 10 are representations of GCMS peaks of 1,3,5-trimethylhexahydro-1,3,5-triazine.
Figure 9:
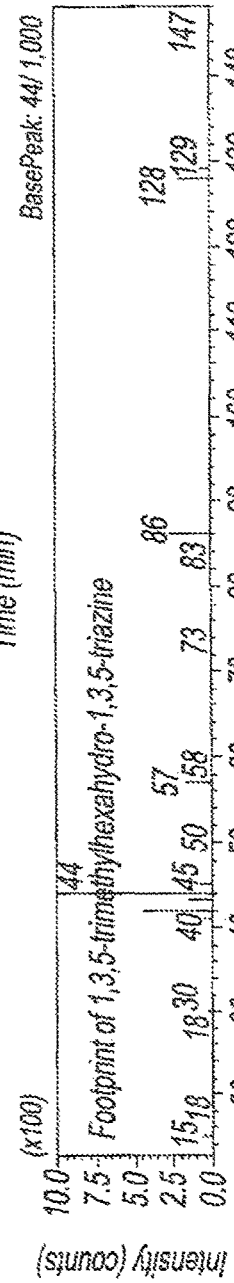
Figure 10:
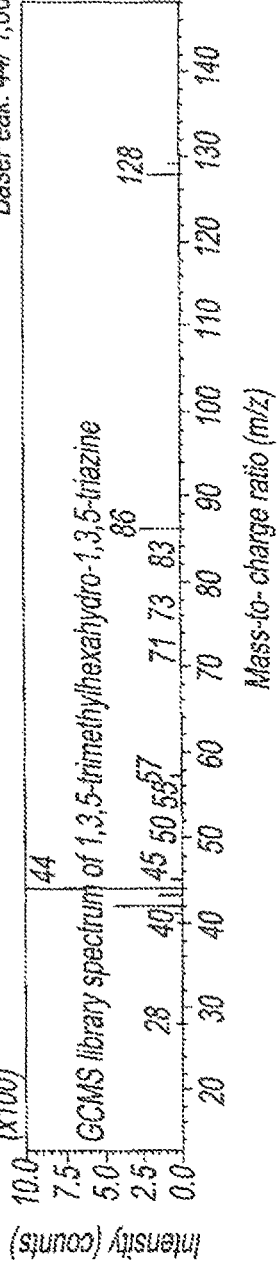

A 1H NMR spectrum for 1,3,5-trimethylhexahydro-1,3,5-triazine as taken from the website of Sigma Aldrich is depicted in FIG. 5. GCMS profiles for 1,3,5-trimethylhexahydro-1,3,5-triazine are shown in FIGS. 8 to 10. Identified GCMS peaks for 1,3,5-trimethylhexahydro-1,3,5-triazine are set forth in Table 1 below.

TABLE 1

| Retention Time (min) | Peak ID |
|---|---|
| 8.3 | Water |
| 9.5 | ethyleneimine (N-methylenemethanamine) |
| 25.4 | ethylene glycol |
| 27.0 | N-methyl formamide |
| 27.3 | 2-methyl-1-butanol |
| 27.4 | N-methyl formamide |
| 28.7 | 1-pentanol |
| 36.1 | NMI |
| 38.8 | 1,4-dimethylimidazole |
| 39.5 | 1,3,5-trimethylhexahydro-1,3,5-triazine |
| 41.2 | 2-octanol |
| 42.4 | 1,2-dimethylimidazole |
| 43.0 | 1-methyl-2-piperidinone |
| 43.7 | 2-methyl-2,4-pentanediamine |
| 45.0 | 1,3-dimethyl-2-(1-methylethyl)cyclopentene |
| 48.1 | hexahydro-1-methyl-1-H-azepin-2-one |

Figure 6:
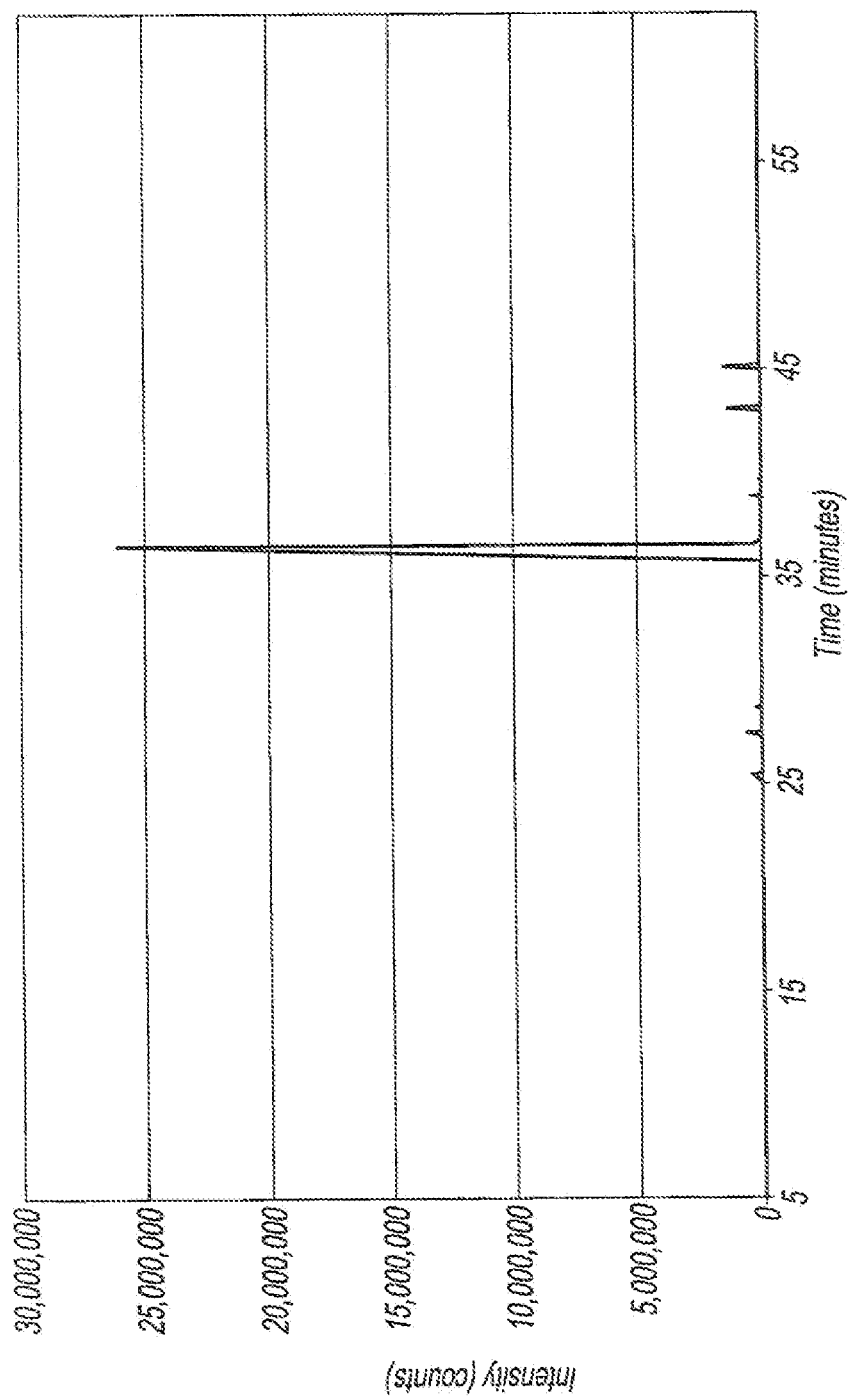
FIGS. 6 and 7 are representations of an impurity profile of an industrial lot of N-methylimidazole obtained via GCMS chromatogram.
Figure 7:
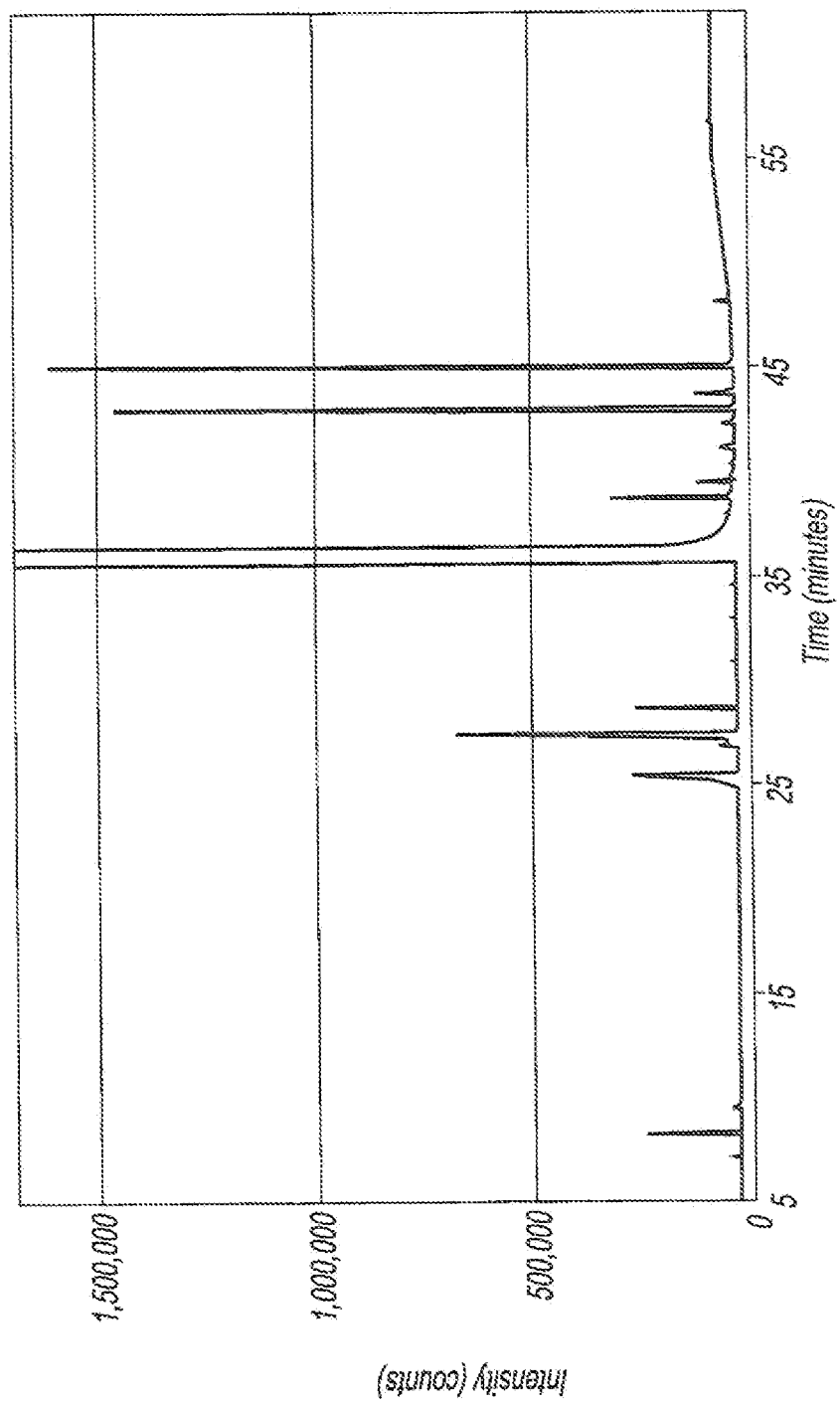

A GCMS Chromatogram showing Total Ion Counts in the NMI is depicted in FIG. 6. A GCMS Chromatogram showing total ion counts on an expanded scale so impurity peaks are visible is depicted in FIG. 7. Data was collected with a Shimadzu GCMS 2010.

Figure 11:
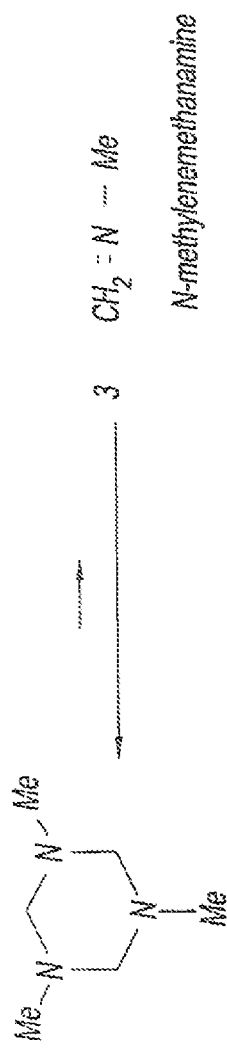
FIG. 11 is a representation of 1,3,5-trimethylhexahydro-1,3,5-triazine in equilibrium with its Schiff base.

An equilibrium expression of 1,3,5-trimethylhexahydro-1,3,5-triazine and its Schiff base is shown in FIG. 11. The expression was taken from Infrared and NMR Spectroscopic Studies of Hexhydro-1,3,5-Trialkyltriazines, Chemia Stosowana (1973), 17(3), 359-66.

Figure 12:
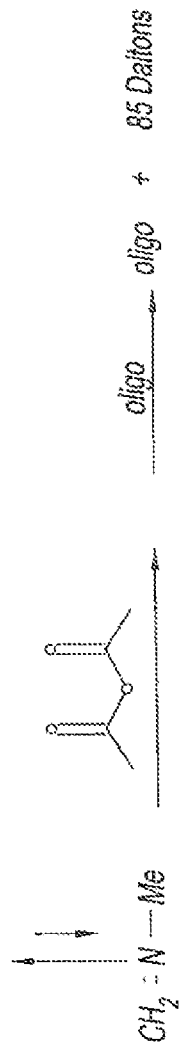
FIG. 12 is a representation of the process of forming an oligonucleotide adduct.

FIG. 12 shows a representation of an oligomerized product of 1,3,5-trimethylhexahydro-1,3,5-triazine.

Example 2

DNA is synthesized according to the procedure and with ingredients set forth in Tables 2 and 3.

TABLE 2

| Detrytilation | Deblock solution |
| Coupling | Activator solution |
| Capping | Capping A & B |
| Oxidation | Oxidation Solution |
| Cleavage | Ammonia (RT) |
| Deprotection | Ammonia (@ 65° C.) |
| Purification | HPLC (Buffers) |

TABLE 3

| Reagent | Formulation |
|---|---|
| Detritylation Solution | 3.0% Dichloroacetic Acid in Dichloromethane (v/v) |
| Detritylation Solution | 3.0% Dichloroacetic Acid in Toluene (v/v) |
| ETT Activator | 0.25M 5-Ethylthio-1H-tetrazole (ETT) in Acetonitrile |
| BMI Activator | 0.3M BMT with 0.5% NMI in acetonitrile |
| Oxidation Solution | 0.05M Iodine in 90% Pyridine and 10% Water (v/v) |
| Capping A Solution | 20% N-methylimidazole and 80% Acetonitrile (v/v) |
| Capping B Solution | 20% Acetic Anhydride, 30% 2,6-Lutidine and 50% Acetonitrile (v/v/v) |
| Scavenger for Acrylonitrile | 20% Diethylamine in acetonitrile (v/v) |

Figure 13:
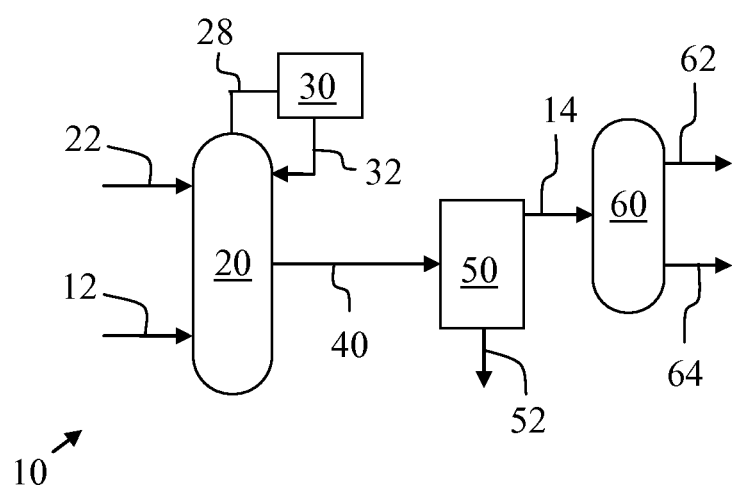
FIG. 13 is a schematic drawing of a method for removing 1,3,5-trimethylhexahydro-1,3,5-triazine from N-methylimidazole.

Referring to FIG. 13, an apparatus 10 and method for removing 1,3,5-trimethylhexahydro-1,3,5-triazine and N-methylenemethanamine from a feedstock 12 containing N-methylimidazole to form a triazine-free product 14 are provided. As shown, the apparatus 10 includes a chamber 20 for receiving the feedstock 12 of impure N-methylimidazole. In certain embodiments, the feedstock 12 of impure N-methylimidazole may have a 1,3,5-trimethylhexahydro-1,3,5-triazine concentration of about 20 parts per million (ppm) to about 1500 ppm, such as about 400 ppm to about 1000 ppm, for example about 475 ppm.

The chamber 20 further receives molecular sieves 22. The molecular sieves 22 may be positioned in the chamber 20 before or after the feedstock 12 in a batch process. In an exemplary embodiment, the molecular sieves 22 are small or medium pore acidic molecular sieves, i.e., sieves with a pore aperture size of no more than about 0.65 nanometer (nm). Exemplary molecular sieves have a pore aperture size of less than about 0.6 nm, for example about 0.54 nm or about 0.42 nm or about 0.38 nm. Pore aperture size refers to the size of the largest pore in a molecular sieve, for example, the largest diameter or dimension across the largest pore.

The molecular sieves 22 may include zeolites or synthetic molecular sieves. Synthetic molecular sieves include aluminophosphates (family of $AlPO_4$ structures); silicoaluminophosphates (SAPO family); various metal-substituted aluminophosphates [MeAPO family, such as CoAPO-50 (AFY)]; and other microporous framework structures, such as crystalline silicotitanates. Zeolites have the chemical formula $M_{2/n}OAl_2O_3 \cdot xSiO_2 \cdot yH_2O$, where the charge-balancing nonframework cation M has valence n, x is 2.0 or more, and y is the moles of water in the voids. The Al and Si tetrahedral atoms, or T-atoms, form a three-dimensional framework of $AlO_4$ and $SiO_4$ tetrahedra linked together by shared oxygen ions. Although a $SiO_4$ tetrahedra is charge-balanced, an $AlO_4$ tetrahedra has a negative charge balanced by a positive charge on M. Related pure $SiO_2$ frameworks, such as silicalite-1, are charge-balanced and do not need non-framework cations. Variants may involve Ge substitution for Si in the framework or involve substitution of Fe, Co, Mn, Zn, Ti, or Mg for Al. In the related aluminophosphates ($AlPO_4$), each negatively charged $AlO_4$ tetrahedron is balanced by a positively charged $PO_4$ tetrahedron, and nonframework cations are not needed. For silicoaluminophosphate (SAPO) structures, Si substitutes some P in the $AlPO_4$ framework. Each added Si in SAPO structures needs a nonframework cation to balance the charge on the framework.

The pore geometry and volume in a molecular sieve is determined by the specific topology of the particular three dimensional framework. The lower the T-atom density per volume of the zeolite crystal, the higher the void fraction inside the crystal. The size of the largest pore in a zeolite is determined by the number of oxygen ions rimming the pore and its shape; e.g. a planar, circular eight-ring (8R) pore rimmed by eight oxygen ions has a diameter of 0.41 nm, as in Linde Type A zeolite, whereas the elliptical 8R pore of NaP zeolite (GIS) is 4.5×0.31 nm.

In an exemplary embodiment, the molecular sieves 22 are SAPO-34. Such an exemplary molecular sieve has a chabazite framework (CHA) and is a 3-dimensional 8-membered-ring molecular sieve. The exemplary molecular sieve has a cage size of from about 0.4 nm to about 0.8 nm, such as about 0.63 nm. In certain embodiments, the molecular sieve has a channel diameter of 0.38 nm. The exemplary molecular sieve has the chemical formula $(SiO_2)_x(Al_2O_3)_y(P_2O_5)_z$. The exemplary molecular sieve has a specific surface area of more than about 400 to about 2000 square meters per gram ($m^2/g$), such as at least about 550 $m^2/g$. The exemplary molecular sieve has a pore volume of at least about 0.2 cubic centimeters per gram ($cm^3/g$), such as at least about 0.27 $cm^3/g$. The exemplary molecular sieve has an average particle size of about 0.3 micrometers (μm) to about 5.0 μm, such as about 2 μm to about 4 μm. The exemplary molecular sieve is about 5 wt % to about 20 wt % $SiO_2$, such as about 8 wt % $SiO_2$ to about 15 wt % $SiO_2$. The exemplary molecular sieve is about 30 wt % to about 50 wt % $Al_2O_3$, such as about 42 wt % $Al_2O_3$.

In another exemplary embodiment, the molecular sieves include ferrierite (FER). The exemplary molecular sieves have an 8-ring channel with a cross-section of 0.35×0.48 nm and a 10-ring channel with a cross-section of 0.42×0.54 nm. The ferrierite has a Si/Al molar ratio of about 5 to about 50. The molecular sieve may be bound with an inorganic binder such as alumina, silica or clay.

In FIG. 13, the feedstock 12 and the molecular sieves 22 are contacted in the chamber 20 and are heated. In an exemplary embodiment, the molecular sieves 22 and the feedstock 12 are contacted in a ratio between about 0.5 grams (g) of molecular sieves per 100 milliliters (ml) of feedstock to about 8 g of the molecular sieves per 100 ml of feedstock, for example about 2.5 g of the molecular sieves per 100 ml of feedstock. The mixture of the feedstock 12 and the molecular sieves 22 may be heated to a temperature suitable for the adsorption of 1,3,5-trimethylhexahydro-1,3,5-triazine from the feedstock 12 by the molecular sieves. For example, the mixture is heated to at least 150° C., such as to at least 200° C., for example to about 204° C. In an exemplary embodiment, the mixture is heated to its boiling point to form a vapor stream 28. As shown, the vapor stream 28 exits the chamber 20 and is delivered to a condenser 30. A condensed liquid stream 32 is formed by the condenser 30 and is returned to the chamber 20 in a reflux loop.

In a batch process, the mixture is heated at the desired temperature for at least about 3 minutes, such as for about 5 to about 10 minutes. Thereafter, the heated mixture 40 of the feedstock and the molecular sieves is removed from the chamber 20 and is delivered to a separation unit 50, such as for example a filter. The separation unit 50 separates the triazine-free product 14 as a supernatant from the triazine-rich molecular sieves 52. In an exemplary embodiment, the separation unit 50 separates the triazine-free product 14 from the triazine-rich molecular sieves 52 when the heated mixture 40 is still hot, i.e., at least about 120° C., such as at least about 150° C. or after it has cooled to room temperature. As used herein "triazine-free" refers to a content of triazine of no more than about 20 ppm. In certain embodiments, the apparatus 10 forms a triazine-free product 14 having a triazine content of no more than about 10 ppm, such as no more than about 5 ppm or no more than about 1 ppm.

As shown in FIG. 13, the apparatus 10 may further include a fractionation unit 60, such as a distillation column. The fractionation unit 60 receives the triazine-free product 14 and fractionates it into streams 62 and 64 for further isolation of N-methylimidazole in a selected stream and removal of contaminants in the other stream.

The features of the method for removing 1,3,5-trimethylhexahydro-1,3,5-triazine from N-methylimidazole will be made more apparent by the following examples, which are not to be construed as limiting.

Example 3

2 g of SAPO-34 molecular sieves were added to 200 mL of N-methylimidazole containing 830 ppm 1,3,5-trimethylhexahydro-1,3,5-triazine in a round bottom flask. The flask was heated to a selected temperature and was maintained at that temperature for 5 to 10 minutes. Then an aliquot of the N-methylimidazole was removed to test for the remaining concentration of 1,3,5-trimethylhexahydro-1,3,5-triazine. The results for each selected temperature are provided in TABLE 4:

TABLE 4

| Temperature (° C.) | Triazine Concentration (ppm) |
| --- | --- |
| 65 | 694 |
| 100 | 407 |
| 130 | 213 |
| 150 | 63 |
| 204 (reflux) | <20 |

Example 4

5 g of SAPO-34 molecular sieves were added to a round bottom flask of 200 mL of N-methylimidazole containing 475 ppm 1,3,5-trimethylhexahydro-1,3,5-triazine (as determined by GCMS). The flask was heated to boiling (204° C.) and refluxed for 5 minutes. The molecular sieves were then filtered off and the remaining supernatant was brownish-orange in color. GCMS detected no triazine in the supernatant, i.e., the triazine concentration was less than 20 ppm. The supernatant was distilled to form a clear and colorless fraction of N-methylimidazole. GCMS detected no triazine in the fraction of N-methylimidazole, i.e., the triazine concentration was less than 20 ppm.

Example 5

5 g of Ferrierite molecular sieves were added to a round bottom flask of 200 mL of N-methylimidazole containing 1100 ppm 1,3,5-trimethylhexahydro-1,3,5-triazine (as determined by GCMS). The flask was heated to boiling (204° C.) and refluxed for 5 minutes. The molecular sieves were then filtered off and the remaining supernatant was brownish-orange in color. GCMS detected a reduced amount of triazine in the supernatant, i.e., the triazine concentration was less than 250 ppm. The supernatant was distilled to form a clear and colorless fraction of N-methylimidazole. GCMS detected a reduced amount of triazine in the fraction of N-methylimidazole, i.e., the triazine concentration was less than 250 ppm.

As described herein, methods for removing triazine from N-methylimidazole and for using triazine-free N-methylimidazole in the synthesis of oligonucleotide have been provided. In exemplary embodiments, impure N-methylimidazole is contacted with molecular sieves and heated such that triazine is adsorbed from the N-methylimidazole by the molecular sieves.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the claimed subject matter in any way. Rather, the foregoing detailed description will provide those skilled in the art with a convenient road map for implementing an exemplary embodiment or embodiments. It being understood that various changes may be made in the function and arrangement of elements described in an exemplary embodiment without departing from the scope set forth in the appended claims.

What is claimed is:

1. A method for removing 1,3,5-trimethylhexahydro-1,3,5-triazine and N-methylenemethanamine from a feedstock containing N-methylimidazole, the method comprising:
    contacting the feedstock with small or medium pore molecular sieves, wherein the small or medium pore molecular sieves adsorb 1,3,5-trimethylhexahydro-1,3,5-triazine and N-methylenemethanamine from the feedstock; and
    separating the small or medium pore molecular sieves from the feedstock.

2. The method of claim 1 wherein contacting the feedstock with small or medium pore molecular sieves comprises contacting the feedstock with synthetic molecular sieves having a pore aperture size of no more than about 0.6 nm.

3. The method of claim 2 wherein contacting the feedstock with small or medium pore molecular sieves comprises contacting the feedstock with silicoaluminophosphate (SAPO) molecular sieves.

4. The method of claim 3 wherein contacting the feedstock with small or medium pore molecular sieves comprises contacting the feedstock with SAPO-34 molecular sieves.

5. The method of claim 1 wherein contacting the feedstock with small or medium pore molecular sieves comprises:
    mixing the feedstock with the small or medium pore molecular sieves in a chamber,
    heating the chamber to form a reflux of condensed vapor, and
    returning the reflux to the chamber.

6. The method of claim 1 further comprising the step of heating the small or medium pore molecular sieves and the feedstock to the boiling point of the feedstock for at least about 3 minutes.

7. The method of claim 1 wherein separating the small or medium pore molecular sieves from the feedstock forms a supernatant containing the N-methylimidazole, and wherein the method further comprises fractionating the supernatant to obtain an N-methylimidazole product.

8. The method of claim 1 wherein the feedstock has a 1,3,5-trimethylhexahydro-1,3,5-triazine and N-methylenemethanamine concentration of about 200 parts per million (ppm) to about 1100 ppm, and wherein separating the small or medium pore molecular sieves from the feedstock comprises isolating a supernatant with a 1,3,5-trimethylhexahydro-1,3,5-triazine and N-methylenemethanamine concentration of about 0 ppm to about 20 ppm.

9. The method of claim 1 wherein contacting the feedstock with small or medium pore molecular sieves comprises contacting the small or medium pore molecular sieves with the feedstock in a ratio between about 0.5 grams (g) of the small or medium pore molecular sieves per 100 milliliters (ml) of feedstock to about 8 g of the small or medium pore molecular sieves per 100 ml of feedstock.

10. The method of claim 1 wherein contacting the feedstock with small or medium pore molecular sieves comprises contacting the small or medium pore molecular sieves with the feedstock in a ratio of about 2.5 grams (g) of the small or medium pore molecular sieves per 100 milliliters (ml) of feedstock.

* * * * *